United States Patent [19]

Burgess et al.

[11] Patent Number: 4,818,361

[45] Date of Patent: Apr. 4, 1989

[54] COMBINED PH AND DISSOLVED CARBON DIOXIDE GAS SENSOR

[75] Inventors: Bruce Burgess, Ann Arbor, Mich.; Glenn Martin, Newark, Del.

[73] Assignee: Diamond Sensor Systems, Ann Arbor, Mich.

[21] Appl. No.: 126,438

[22] Filed: Nov. 30, 1987

Related U.S. Application Data

[63] Continuation-in-part of Ser. No. 940,527, Dec. 10, 1986, abandoned.

[51] Int. Cl.$^4$ ............................................... G01N 27/30
[52] U.S. Cl. ................................... 204/406; 204/411; 204/412; 204/415; 204/433
[58] Field of Search ............... 204/406, 409, 411, 412, 204/415, 433

[56] References Cited

U.S. PATENT DOCUMENTS 3,896,020  7/1975  LeBlanc ........................ 204/415 X
4,225,410  9/1980  Pace ................................... 204/412
4,734,184  3/1988  Burleigh et al. ................... 204/409

OTHER PUBLICATIONS

D. Ammann et al, Ion–Selective Electrode Reviews, vol. 5, p. 38, (1983).

Primary Examiner—G. L. Kaplan
Attorney, Agent, or Firm—Krass & Young

[57] ABSTRACT

A combination pH and $CO_2$ sensor employs separate sensors. Each sensor has a wire with an electrochemically active layer, an electrolyte layer and a membrane between the electrolyte layer and the fluid to be tested. Each electrolyte layer is constructed of a dried residue which can be easily stored and which must be rehydrated prior to the first use. The electrolyte layer in the pH sensor when hydrated forms an aqueous solution buffered against changes in pH due to changes in the dissolved $CO_2$ concentration and is preferably formed of 2-(n-morpholino) ethanesulfonic acid, 2-(n-morpholino) ethanesulfonic acid - sodium salt and potassium chloride. The electrolyte layer in the $CO_2$ sensor when hydrated forms an aqueous solution having bicarbonate ions and is preferably formed of polyvinyl alcohol, sodium chloride and sodium bicarbonate. The electrical potential at the pH sensor is proportional to the pH of the fluid. The electrical potential difference between the $CO_2$ sensor and the pH sensor is proportional to the concentration of dissolved $CO_2$ in the fluid. In the preferred embodiment the two sensors are formed in a sensor assembly with the fluid pumped through a channel. This invention is readily adaptable to a storage stable disposable assembly.

16 Claims, 4 Drawing Sheets

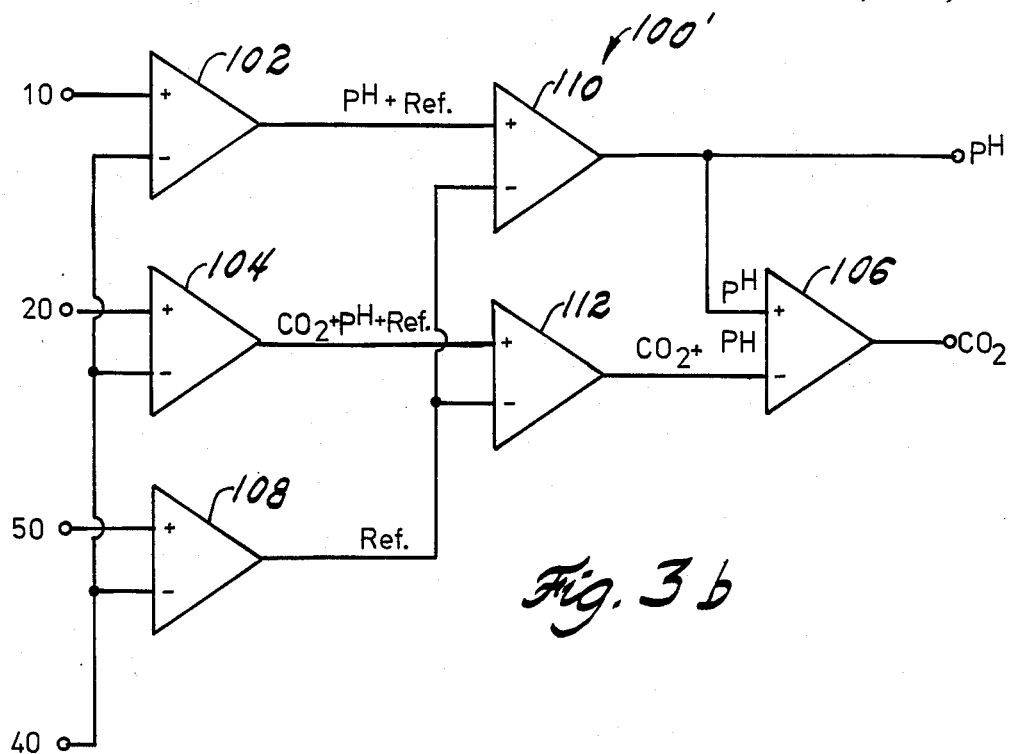
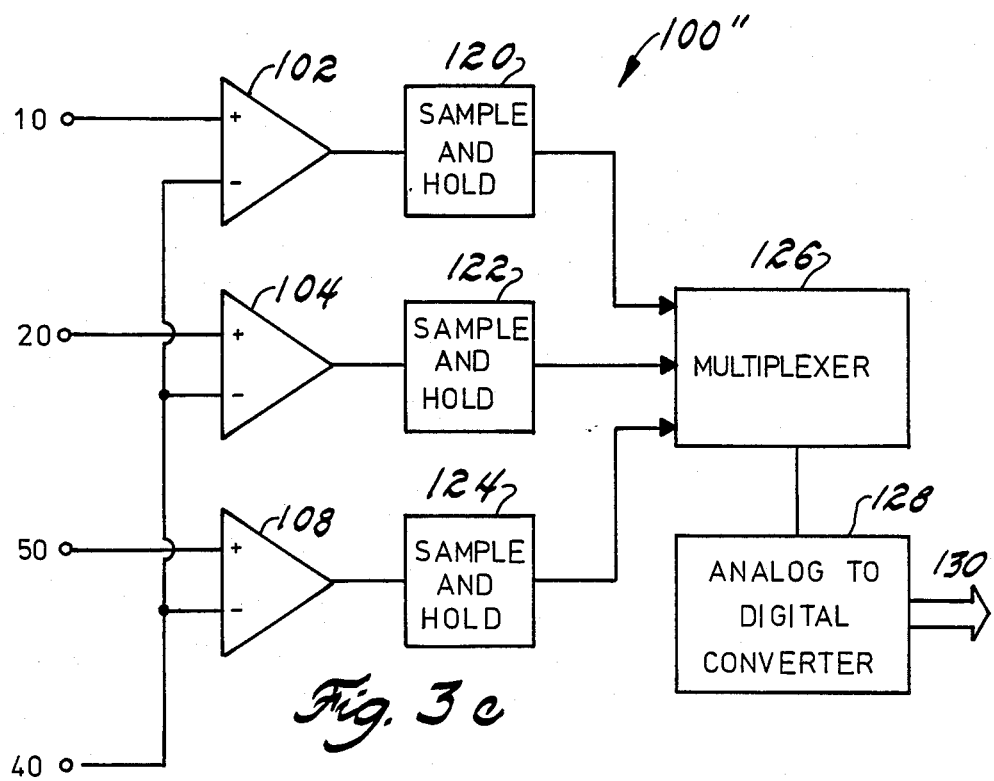

COMBINED PH AND DISSOLVED CARBON DIOXIDE GAS SENSOR

RELATED APPLICATION

This application is a continuation-in-part of U.S. patent application Ser. No. 940,527, filed Dec. 10, 1986, now abandoned.

FIELD OF THE INVENTION

This invention relates to solid state electrode or sensor apparatus and technology for measuring the dissolved carbon dioxide concentration of an aqueous sample such as a body fluid or a blood sample and more particularly to such apparatus of the kind which employs storage-stable hydratable sensors for measuring this characteristic.

BACKGROUND OF THE INVENTION

In a variety of clinical situations it is important to measure certain chemical characteristics of the patient's blood such as pH, concentrations of calcium, potassium ions and hematocrit, the partial pressure of $O_2$ and $CO_2$ and the like. (See, for example, Fundamentals of Clinical Chemistry, Tietz, Editor, page 135 et seq., Electrochemistry; page 849 et seq., Blood Gases and Electrolytes; 1976, Saunders Company, Phila.; see also the patent to Battaglia et al. U.S. Pat. No. 4,214,968.) These situations range from a routine visit of a patient in physician's office to monitoring during open-heart surgery. The required speed, accuracy, and similar performance characteristics vary with each situation.

Measurement of chemical characteristics of blood during open-heart surgery provides the most demanding set of criteria. Presently, blood gas analysis during major surgery is provided by repeated transfer of discrete blood samples to a permanent lab-based blood gas analyzer or by use of sensors placed in-line with the extra-corporeal blood circuit of a heart-lung machine employed to bypass the patient's heart.

The transfer of discrete blood samples, required by blood-gas analyzers, inherently increases the risk of contaminating the blood sample with ambient air, which may alter certain of the monitored characteristics. Additionally, since such analyzers are complex and costly devices, they are typically located only in the hospital lab where they need to be operated by a skilled technician, resulting in undesirable delay during surgery, critical care or intensive care. Further, such analyzers employ bubble tonometers to generate a suitable gas reference mixture by dissolving quantities of gases, stored in pressurized free-standing tanks, into the electrolyte solution. While replacement of these gas tanks is infrequently required, it is a cumbersome procedure. Finally, these existing analyzers require cleaning to decontaminate all exposed portions from the prior patient's blood prior to subsequent use.

Heretofore measurements of the concentration of dissolved carbon dioxide in body fluids such as blood samples has been carried out using a Stow-Severinghous $CO_2$ electrode. This device operates on the principle that $CO_2$, when dissolved in an aqueous solution containing bicarbonate ions, will alter the pH of that solution in a manner which is proportional to the concentration of the dissolved $CO_2$. A thin film of bicarbonate solution is contained between the chemically sensitive surface of a combination pH electrode, consisting of a pH sensor and a reference sensor, and a gas permeable membrane. When the outer surface of the membrane is surrounded by an aqueous fluid containing dissolved carbon dioxide, the concentration of $CO_2$ dissolved in the thin film of solution will rapidly equilibrate with the $CO_2$ concentration outside of the membrane. The pH of the bicarbonate solution, which is now proportional to the $CO_2$ concentration at the outer surface of the membrane, is measured using the pH sensor internal to the membrane, and thus the device has an electrical output which is proportional to $CO_2$ concentration.

The structure of the Stow-Severinghous $CO_2$ electrode can therefore be summarized as a gas permeable membrane under which is contained a layer of aqueous electrolyte solution containing bicarbonate ions, combined with internal pH and reference electrodes which together measure the pH of the bicarbonate solution, and thus the $CO_2$ concentration. While this device is functionally effective, it is a relatively complex structure. In particular the Stow-Severinghous $CO_2$ electrode is not well adapted to automated manufacture. With the trend in medical appliances and supplies toward disposables, automated manufacture with the accompanying reduction in production costs is believed to be highly advantageous.

A further problem exists with some types of $CO_2$ sensors. In many of these sensors the aqueous electrolyte solution containing bicarbonate ions requires the sensor to be hydrated during storage prior to use. In particular, some of these sensors use a gel to provide the bicarbonate ions. This gel must be kept hydrated in storage prior to use in order to remain useful. It would be advantageous to provide a sensor which can be stored in an anhydrous state to be rehydrated prior to the first use. Such a feature would be particularly advantageous for disposable appliances.

Accordingly there is a need for an inexpensive, easily manufactured electrode assembly for the measurement of dissolved $CO_2$ in body fluids such as blood samples which is storable in an anhydrous state and is adaptable for disposable use. Such a $CO_2$ electrode could be employed in a set of sensor electrodes for the measurement of a variety of chemical characteristics of the sample.

SUMMARY OF THE INVENTION

In a preferred embodiment, the invention concerns a cartridge or sensor device that includes a novel combination of two solid state sensors: a carbon dioxide sensor and a pH sensor. The solid-state carbon dioxide gas sensor device includes a structural body member housing a chamber and has means for introducing an aqueous fluid sample into the chamber for measuring the content of carbon dioxide gas dissolved in a fluid sample thus contained in the chamber. The housing structure comprises a pH sensor and a carbon dioxide gas sensor. Each is positioned so as to be in contact with aqueous fluid sample contained in the chamber without being in direct physical contact with one another. The sensors are electrochemically coupled via an interface layer having, for example, a silver/silver chloride coupling surface. The second end of each sensor extends outside of the housing structure for use with any suitable signal receiving means or analysis means for analyzing the sensor signal. The pH sensor includes an outer gas and water permeable pH sensitive membrane exposed to the chamber and an inner electrolyte layer containing a pH buffer which contacts the pH sensor electrode coupling surface. The carbon dioxide gas sensor includes an outer gas and water permeable pH sensitive membrane exposed to the chamber and an inner electrolyte layer containing bicarbonate ions which contacts the carbon dioxide gas sensor electrode coupling surface. Each of these inner electrolyte layers is constructed as a dry residue and is stored in an anhydrous state. These layers are rehydrated prior to the first use of the sensors. This combination of sensors is capable of electrochemical interaction with the carbon dioxide content of a contained sample for producing a signal which is a function of the carbon dioxide content.

BRIEF DESCRIPTION OF THE DRAWINGS

Advantages of the present invention will be apparent upon reading the following specification and by reference to the drawings in which:

FIGS. 3a to 3c are schematic diagrams showing alternative electrical circuits for generating the signal proportional to the dissolved carbon dioxide gas.

DETAILED DESCRIPTION OF THE INVENTION

A preferred embodiment of the invention is adapted to measure the unbound concentration, or activity, of the single gas, carbon dioxide, and the pH of any of a variety of aqueous fluids.

Figure 1:
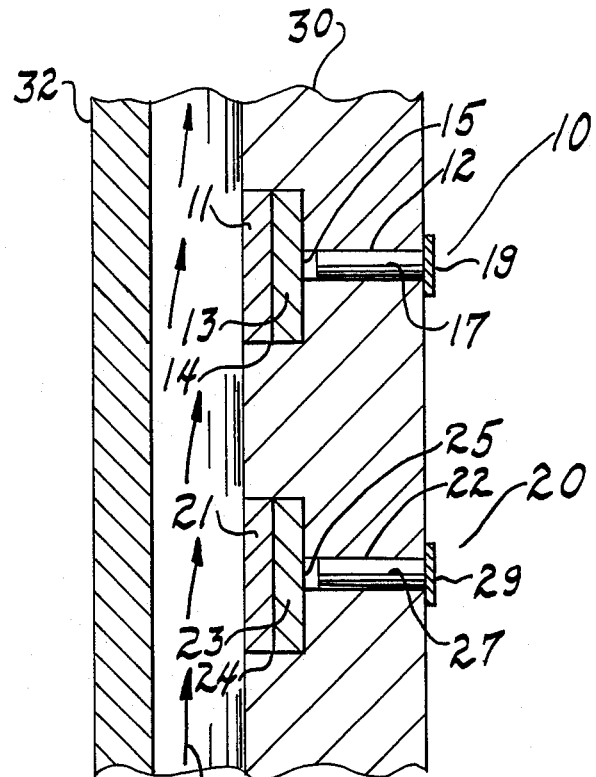
FIG. 1 is a cross-sectional view of the pH sensing electrode and the $CO_2$ sensing electrode of the present invention.

FIG. 1 illustrates the structure of a pair of sensors employed to measure both the pH of the fluid and the dissolved carbon dioxide gas of the fluid. These electrodes are formed in a substrate 30 and communicate with a measurement flow channel 34 which is formed by the combination of substrate 30 and cover plate 32. FIG. 1 illustrates pH sensor 10 and $CO_2$ sensor 20. The pH sensor 10 includes a wire 17 disposed in and substantially filling a hole 12 in the substrate 30. This wire 17 is preferably made of silver. At one end of the wire, the end opposite the measurement flow chamber 34, wire 17 is coupled to electrical conductor 19 which serves as the electrical connection to pH sensor 10. Conductor 19 may be in the form of a printed circuit conductor which lies upon the opposite surface of substrate 30. At the other end of electrode wire 17 is an electrochemically active layer 15. This electrochemically active layer 15 serves to electrochemically couple wire 17 to the electrolyte layer 13. In accordance with the preferred embodiment, electrochemically active layer 15 is formed of silver chloride.

The remaining portions of pH sensor 10 are formed in a shallow well 14 which is preferably concentric about the electrode hole 12. The inner layer 13 is an electrolyte layer which when hydrated forms an aqueous solution which is buffered against changes in pH due to the changes in the dissolved $CO_2$ concentration of the fluid. In accordance with the preferred embodiment, this electrolyte layer is formed from the dried residue of an aqueous solution of 2-(n-morpholino) ethanesulfonic acid, 2-(n-morpholino) ethanesulfonic acid-sodium salt (MES) and potassium chloride. In the preferred embodiment this electrolyte layer is formed of an aqueous solution containing 0.024 molar 2-(n-morpholino ethanesulfonic acid, 0.024 molar MES, and $5.0 \times 10^{-6}$ molar potassium chloride. The outer layer 11 is preferably a membrane which has an outer surface exposed to the fluid in measurement channel 34 and an inner surface which covers the electrolyte layer 13. This membrane must be sensitive to the difference in pH between the inner and outer surfaces thereof to form an electrical potential thereacross and water permeable. In accordance with the preferred embodiment this membrane 11 is formed of the dried residue of a solution of polyvinyl chloride, potassium tetrakis (4-chlorophenyl) borate, bis (2-ethyl hexyl) sebacate and tridodecylamine in an organic solvent. In accordance with "Neutral Carrier Based Ion-Selective Electrodes," by D. Ammann, W. E. Morf, P. Aaker, P. C. Meier, E. Pretsch and W. Simon, Ion-Selective Electrode Reviews, 1983, vol. 5, p. 38, the ingredients are provided in following percentages by weight: 1.0% tridodecylamine; 0.6% potassium tetrakis (4-chlorophenyl) borate; 65.6% bis (2-ethyl hexyl) sebacate; and 32.8% polyvinyl chloride. The organic solvent is preferably tetrahydrofuran (THF). The concentration of the original solution is not critical so long as the proper ratio of solutes is maintained. The concentration can be adjusted to provide the desired viscosity when the solution is disposed in shallow well 14. As thus assembled, the electrical potential difference between conductor 19 and the fluid in measurement flow channel 34 corresponds to the pH of this fluid.

The $CO_2$ sensor 20 is constructed similar to the construction of pH electrode 10. A wire 27 is disposed in and substantially fills a hole 22 made in the substrate 30. A conductor 29 formed on the outer surface of substrate 30 serves as the electrical connection to this wire. An electrochemically active layer 25 serves to electrochemically couple wire 27 to the electrolyte layer 23. In accordance with the preferred embodiment, as noted above, the wire 27 is composed of silver and the electrochemically active layer 25 is composed of silver chloride.

The $CO_2$ sensor 20 also includes a pair of layers 21 and 23 disposed in shallow well 24. Shallow well 24 is preferably concentric about hole 22. The interior layer 23 is an electrolyte layer which when hydrated forms an aqueous solution including bicarbonate ions. This layer could be formed of the dried residue of various salts one of which includes bicarbonate. In accordance with the preferred embodiment, this electrolyte layer is formed of the dry residue of an aqueous solution of polyvinyl alcohol, sodium chloride and sodium bicarbonate. In the preferred embodiment this electrolyte layer is formed of an aqueous solution of 4% (weight/volume) polyvinyl alcohol (115,000 molecular weight, 100% hydrolyzed), 0.005 molar sodium bicarbonate, and 0.0005 molar sodium chloride. The polyvinyl alcohol is employed to control the degree of hydration and stabilize the thickness of this layer upon rehydration. This serves to foster more reproducable sensor performance. Other hydrophylic materials, including but not limited to water soluble polymers and starches, could be employed to achieve the same results. The outer layer 21 is preferably a membrane with the outer surface exposed to the fluid in the measurement flow channel 34 and the inner surface completely covering the electrolyte layer 23. This membrane is sensitive to the difference in pH between the inner and outer surfaces to form an electrical potential thereacross and must be both water and dissolved $CO_2$ permeable. In accordance with the preferred embodiment, membrane 21 is formed in the same manner as membrane 11. That is, membrane 21 comprises the dry residue of a solution of polyvinyl chloride, potassium tetrakis (4-chlorophenyl) borate, bis (2-ethyl hexyl) sebacate and tridodecylamine in an organic solvent.

Figure 2:
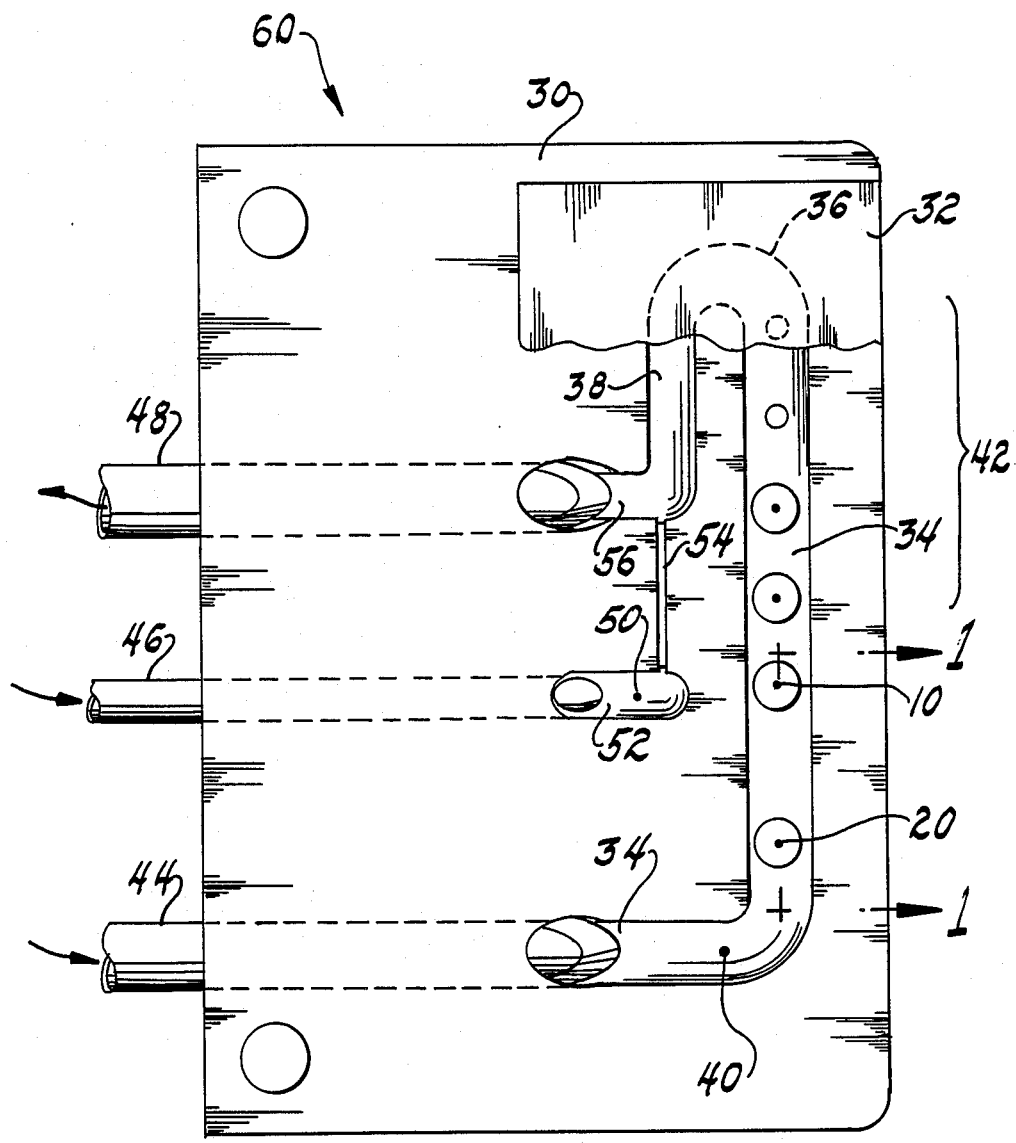
FIG. 2 is a reverse frontal partly fragmentary view of the electrode card.

FIG. 2 illustrates an embodiment of a sensor assembly 60 including the sensors illustrated in FIG. 1. The sensor assembly 60 receives a flow of the reference solution via line 46 and sequential flows of either the blood sample or one of two calibrating solutions via line 44. The sensor assembly 60 also provides a corresponding output of its waste products to a waste collection bag via line 48. The sensor assembly 60 in a preferred embodiment consists of a structurally rigid rectangular plate or substrate 30 of polyvinylchloride having a rectangular aluminum cover plate 32 adhered to one of its surfaces. Cover plate 32 closes off the flow channels formed in one surface of the substrate 30 and also acts as a heat transfer medium to maintain the fluids flowing through the sensor assembly, and the sensors themselves, at a constant temperature. This may be achieved by measuring the temperature of the plate 32 and employing a suitable heating or cooling element to maintain the temperature of the plate at a constant desired level.

The rectangular sensor assembly 60 is intended to be used with its major surfaces and its major axis in the vertical plane and is so supported. The flow line 44 passes through the thickness of plate 30 from the side opposite to the plate 32, near the bottom of the plate 30, at an angle (FIG. 2) with respect to the plates, to communicate with measurement flow channel 34 formed in suitable manner (e.g., machined, molded, or etched) in the surface of the plate 30 that abuts the cover plate 32, so that the abutting surface of the plate 32 forms one wall of the measurement flow channel 34. Near one long edge of the plates 30 and 32 measurement flow channel 34 turns upward and extends parallel to the one long edge of the plates 30 and 32. Near the upper edge of the plate 30 measurement flow channel 34 makes a hair pin (180°) bend inward, away from the edge of the plate, at 36 to form a downwardly extending channel 38 parallel to and spaced from measurement flow channel 34. At its lower end, about ⅓ of the way from the top of the plate, the channel 30 makes a 90° turn to join with a short horizontally extending channel 56. The waste flow line 48 passes through the thickness of the substrate 30 from the side opposite to the cover plate 32 to communicate with the end of the flow channel 56. Thus, blood samples or calibrating solution, pumped into the electrode assembly via line 44, move along flow channel 34, then around the curve of the channel 36 at the top of the assembly, down the channel 38, and finally horizontally along the channel 56 to the output flow line 48 which carries the used fluids to a waste bag.

The provision of measurement flow channel 34 in which the blood and calibrating solutions must flow vertically upward ensures that any microbubbles in the blood or calibrating solution will rise to the space at the top of channel 36 and not interfere with accurate measurements made by the electrodes.

A reference solution is introduced to a reference solution chamber 52 formed in the surface of the substrate 30 in the same manner as the other flow channels and similarly covered by the metal plate 32. A reference solution flow line 46 passes through an inclined hole in reference solution chamber 52. The reference solution chamber is connected to the output section 56 of the flow channel through a very thin capillary channel 54 formed in the surface of the plastic substrate 30 in the same manner as the main flow channels. The capillary channel 54 is straight and substantially shallower and narrower than the main flow channel; its cross section is approximately 0.5 sq. mm. Reference fluid pumped into reference solution chamber 52, via a line 46, fills the reference solution chamber 52, and is forced through the capillary channel 54 where it joins the output stream of fluid passing through the main flow channel section and then flows with it to the waste bag. The combined influence of its higher density and the capillarity of the capillary channel 54 serves to minimize any possibility of calibrating solution or blood passing downward through the capillary section 54 to the reference solution chamber 52 and upsetting the electrochemical measurements.

As a blood sample or calibration solution is introduced into measurement flow channel 34 and passes to the output section 56, it passes over a number of electrodes. These include ground electrode 40, which is a silver wire staked in a hole in substrate 30, pH sensor electrode 10 and $CO_2$ sensor electrode 20, constructed as described above. These may also include a number of other electrodes (noted generally by 42) for measuring other electrochemical characteristics of the fluid in the measurement flow channel 34. Finally, an electrode 50 is staked through the thickness of the substrate 30 into the reference solution chamber 56 to act as a reference electrode.

As has been noted, the reference solution fills the reference chamber 52 where it contacts a silver wire 50 and is pumped through the capillary channel 54 to join the outlet section 56. The reference solution is essentially a hypertonic solution of potassium chloride, with respect to the blood or the calibrating solutions and accordingly the domain of the reference electrode 50 constitutes a stable potential liquid junction formed between the reference electrode and the blood or calibrating solution, thereby establishing an environment that is independent of the ionic activity of the blood or calibrating solution.

Since the reference solution joins the main flow channel downstream from the electrodes, after the gas/electrolyte measurements have been made, it does not affect those measurements in any way. The reference solution is of high density and under pumping force must flow upward against gravity to the outlet. Thus, when the pump stops, as for electrode equilibration, the reference solution remains stationary in the reference solution chamber 52 and the capillary channel 54 and tends not to diffuse into the calibrating solution or blood in the main flow channel. Thus, the capillary channel 54 due to the density gradient, acts as a one way valve allowing pumped reference solution to pass upwardly through the capillary channel but preventing unwanted reverse passage or mixing of the blood or calibrating solution into the reference well.

Figure 3A:
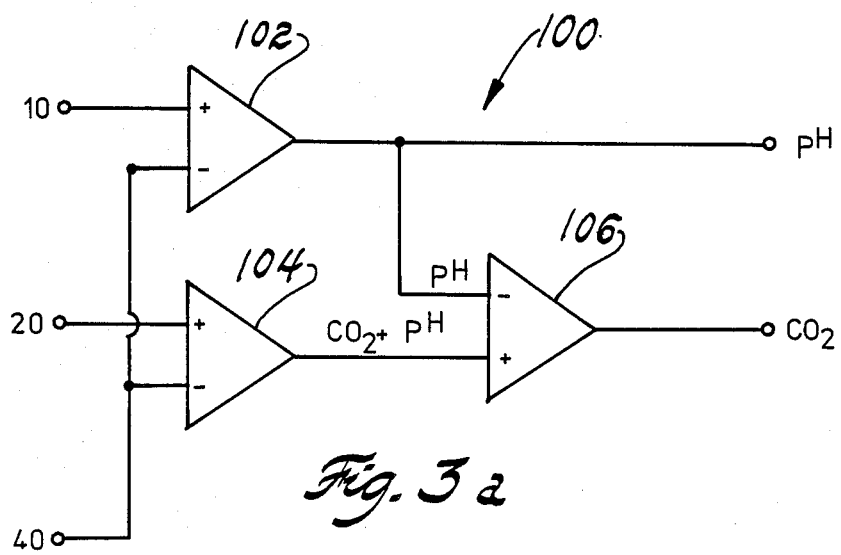

FIGS. 3a, 3b and 3c illustrate alternative connections for the measurements made with pH sensor 10 and $CO_2$ sensor 20. FIG. 3a illustrates a simple system without the use of a reference electrode. FIG. 3b illustrates the use of a reference electrode. FIG. 3c illustrates the use of a reference electrode, a multiplexer and an analog-to-digital converter.

FIG. 3a illustrates the simplest circuit for generating the respective pH signal and the $CO_2$ signal. Differential amplifier 102 has its positive input connected to pH sensor 10 and its negative input connected to ground electrode 40. Similarly, differential amplifier 104 has its positive input connected to $CO_2$ sensor 20 and its negative input connected to ground electrode 40. The output of differential amplifier 102 is the pH signal. The output of differential amplifier 102 is applied to the negative input of differential amplifier 106. In accordance with the theory of operation of the $CO_2$ sensor 20, the output of differential amplifier 104 is a signal proportional to both the dissolved carbon dioxide and the pH of the solution. This signal is applied to the positive input by differential amplifier 106. Differential amplifier 106 forms a difference between these signals and thus removes the pH dependence of the signal from differential amplifier 104. Differential amplifier 106 also removes from the $CO_2$ signal any dependence upon the electrical potential at ground electrode 40. Any of several common types of electrochemical reference electrodes known in the art can be substituted for the ground electrode 40 described herein. The output of differential amplifier 106 is the difference in electrical potential between the $CO_2$ sensor 20 and pH sensor 10. Therefore the output of differential amplifier 106 is the desired $CO_2$ signal.

FIG. 3b illustrates electrical circuit 100' showing the use of reference electrode 50. Reference electrode 50 is employed to provide a highly stable reference potential relative to ground electrode 40 which may drift or shift potential when the properties of the fluid in chamber 36 changes in order to correct for any electrochemical drift in the signals at the pH sensor 10 and the $CO_2$ sensor 20. Differential amplifiers 102 and 104 are connected as illustrated before in FIG. 3a. Differential amplifier 108 has the signal at reference electrode 50 connected to its positive input and the signal from ground electrode 40 connected to its negative input. Differential amplifier 110 has the output of differential amplifier 102 connected to its positive input and the output of differential amplifier 108 connected to its negative input. Differential amplifier 110 thus removes any ground potential voltage drift from the pH signal. This ground potential voltage drift is measured by the reference electrode 50. In a similar fashion, differential amplifier 112 has the output of differential amplifier 104 connected to its positive input and the output of differential amplifier 108 connected to its negative input. The output of differential amplifier 112 is the combined carbon dioxide and pH signal with the ground potential drift removed. Differential amplifier 106 is connected as illustrated in FIG. 3a in order to derive at its output the $CO_2$ signal dependent only upon the concentration of dissolved carbon dioxide in the fluid.

FIG. 3c illustrates electrical circuit 100" suitable for use with a digital processing system. Differential amplifiers 102, 104 and 108 are connected to the electrodes in the manner previously illustrated in FIG. 3b. The output of differential amplifier 102 is connected to sample and hold circuit 120. Similarly, the output of differential amplifier 104 is connected to sample and hold circuit 122 and the output of differential amplifier 108 is connected to sample and hold circuit 124. Each sample and hold circuit serves to detect the output of its respective differential amplifier at a particular sample time and to hold that output until the next sample time. The output of the sample and hold circuits 120, 122 and 124 are separately applied to multiplexer 126. Multiplexer 126 serves to connect the output of one of the sample and hold circuits 120, 122 or 124 to analog-to-digital converter 128. Analog-to-digital converter 128 generates a digital signal corresponding to the magnitude of the analog signal connected thereto. Therefore the output 130 of analog-to-digital converter 128 is a series of digital numbers corresponding to respective measurements of the electrical potential at pH sensor 10, $CO_2$ sensor 20 and reference electrode 50. The embodiment illustrated in FIG. 3c of electrical circuit 100" is employed with a digital processing circuit, such as a microprocessor, which performs the subtraction operation in a digital domain similar to the subtraction operations performed by differential amplifiers 106, 110 and 112.

Figure 4:
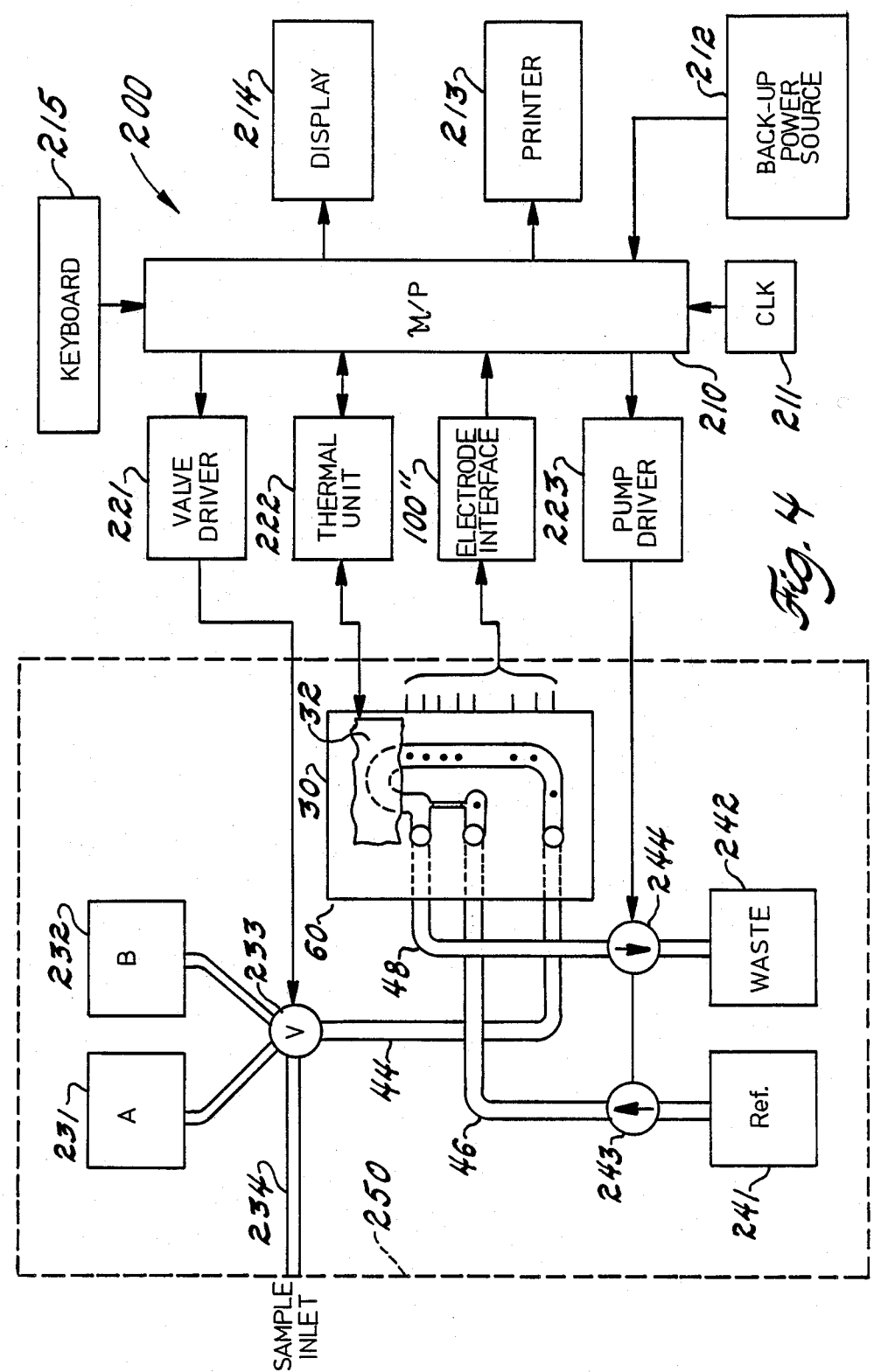
FIG. 4 is a schematic diagram showing the major components of a preferred embodiment of the carbon dioxide gas analysis system of the present invention.

Referring to FIG. 4, the overall system generally indicated at 200 incorporates a microprocessor to control measurement and display of the dissolved carbon dioxide. Blood samples to be analyzed by the system are introduced through a conduit 234. These blood samples are preferably derived on a periodic basis from an extracorporeal blood flow circuit connected to a patient during open heart surgery. The nature of this extracorporeal circuit and the manner in which blood samples may be introduced into the analysis system of the present invention is disclosed in co-pending patent application Ser. No. 713,435, now abandoned, entitled "Apparatus For Chemical Measurement of Blood Characteristics," assigned to the assignee of the present invention and the disclosure of that co-pending application is incorporated herein by reference. Alternatively, blood samples may be introduced into the flow line 234 through other automatic means, or manually, as by syringe. The blood samples may be introduced as discrete samples, as described above.

The system incorporates two prepackaged containers 231 and 232 each containing calibrating aqueous solutions having known values of the parameters to be measured by the system. The two calibrating solutions have different known values of each of the measured parameters to allow the system to be calibrated on a 2-point basis. For purposes of reference the solution contained within the bag 231 will be termed Calibrating Solution A and the solution contained within the bag 232 will be referred to as Calibrating Solution B. Each of the bags 231 and 232 contains a sufficient quantity of its calibrating solution to allow the system to be calibrated a substantial number of times before the cartridge 250 containing the containers must be replaced.

The container 231 is connected to a first input of a 3-position valve 233 and the container 232 for calibration solution B is connected to a second input of the 3-position valve. The blood sample flow inlet 234 is connected to a third input of the three-position valve. The valve 233 is adapted to connect the input flow from either container 231, container 232 or inlet 234 to an output flow line 44, depending upon the position of the valve. The flow line 44 extends to the input of the sensor assembly 60. The position of valve 233 is controlled by microprocessor 210 via valve driver 221.

The system includes a third container 241 for a reference solution. The container 241 is connected to the sensor assembly 60 by a flow line 46. Pump 243 causes the reference solution in container 241 to flow to sensor assembly 60. The system further includes a fourth container 242 for waste, which receives the blood samples, the calibrating solutions and the reference solution after they have passed through the sensor assembly 60, via a flexible conduit 48 that has input from the plate 30. Pump 244 causes flow from the source selected by valve 233, through the sensor assembly 60 into waste container 242.

Both pumps 243 and 244 are preferably sections of flexible walled tubing that pass through a peristaltic pump. Such a pump compresses and strokes the flexible sections of the flow lines 46 and 48 to induce a pressured flow. Pump 244 creates a negative pressure on the waste products in flow line 48 so as to draw fluids in the flow line 44 through passages in the sensor assembly 60. This arrangement, as opposed to the alternative of inducing positive pressure on the blood and calibrating solutions to force them through the sensor assembly 60, avoids the imposition of unnecessary and possibly traumatic mechanical forces on the blood sample and minimizes possibilities of leaks in the electrode assembly.

The system as heretofore described in a preferred embodiment of the present invention is contained in a disposable cartridge 250. A cartridge of a similar type is set forth in detail in the co-pending patent application referred to above. The cartridge 250 contains sufficient quantities of the calibrating solutions and the reference solution to perform analysis of a number of samples of blood. This cartridge 250 also includes the valve 233, the electrode assembly 30 and waste container 242. After use, the cartridge 250 is intended to be discarded and replaced with another cartridge 250.

The sensor assembly 60 has a number of edge connectors in a bank which allow it to be plugged into a female matching connector so that the electrodes formed on the sensor assembly 60 may be connected to microprocessor 210. The microprocessor 210 is connected to the valve 233 via valve driver 221 and to the peristaltic pumps 243 and 244 via pump driver 223. Microprocessor 210 controls the position of the valve 233 and the energization of the pumps 243 and 244 to cause sequences of blood samples and calibrating solutions to be passed through the electrode assembly. When the calibrating solutions are passed through the sensor assembly 60 the sensors forming part of the assembly make measurements of the parameters of the sample and microprocessor 210 stores these electrical values. Based upon measurements made during the passage of the calibration solutions through the electrode assembly, and the known values of the measured parameters contained within the calibrating solution, microprocessor 210 effectively creates a calibration curve for each of the measured parameters so that when a blood sample is passed through the sensor assembly 60 the measurements made by the sensors can be used to derive accurate measurements of the parameters of interest. These parameters are stored, the corresponding quantities calculated and displayed by microprocessor 210 and displayed via display 214 and/or printer 213.

The microprocessor 210 is preferably suitably programmed to perform measurement, calculation, storage and control functions, all as described in co-pending application referred to previously.

When the sensor assembly 60 and the calibration solutions A and B and the reference solution are first used, the valve 233 is controlled to direct one of the calibration solutions into the sensor assembly so it entirely fills the flow channel and is void-free. The pump is then stopped for a period (e.g., 30 minutes) during which the electrodes are allowed to stabilize in the electrode solution. This stabilization includes the rehydration of the dried electrolyte layer 13 of pH sensor 10 and the dried electrolyte layer 23 of $CO_2$ sensor 20. This rehydration is required for proper operation of these sensors and thus the stabilization period prior to first use is necessary. After the stabilization, a predetermined quantity of new calibration solution A is pumped into and through the sensor assembly 60 and during a dwell period (e.g., 90-second dwell) measurements of the various potentials and currents are made and processed by the microprocessor 210. Next, a predetermined quantity of calibration solution B is pumped into and through the sensor assembly 60 while, during a like dwell, similar measurements are made. The blood sample from inlet 234 is then pumped into the sensor assembly 60 while analogous measurements are made and, based on the measurements of the blood sample and the stored measurements, microprocessor 210, with suitable allowance permitted by 2-point calibration, generates the gas/electrolyte values characteristic for the particular blood sample.

This process may be repeated a number of times, either automatically or manually using discrete blood samples under operator control, all within the operating theater or at bedside, to derive quantitative parameters for any of a series of blood samples over a period of time, until the solutions have been depleted, at which time the spent cartridge can be discarded and replaced with a fresh one. It is particularly advantageous for these disposable cartridges to employ pH and $CO_2$ sensors which include dry stored electrolyte layers that are rehydrated prior to first use. This enhances the ease of storage of these cartridges because the electrolyte layers need not be continuously hydrated during storage.

We claim:

1. An apparatus for measuring pH and the concentration of dissolved $CO_2$ in a fluid comprising:
    a measurement chamber for containing a sample of fluid to be measured;
    a pH sensor including
        a first wire having first and second ends, said first end exposed for electrical contact thereto,
        a first electrochemically active layer disposed covering said second end of said first wire for forming an electrochemical coupling to said first wire,
        a first dried electrolyte layer disposed covering said first electrochemically active layer, said first dried electrolyte layer when hydrated forming an aqueous solution buffered against changes in pH due to changes in dissolved $CO_2$ concentration, and
        a first membrane having an outer surface exposed to the fluid in the said measurement chamber and an inner surface covering said first electrolyte layer, said first membrane being sensitive to the difference in pH between the inner and outer surfaces thereof to form an electrical potential thereacross and being water permeable;
    a $CO_2$ sensor including
        a second wire having first and second ends, said first end exposed for electrical contact thereto,
        a second electrochemically active layer disposed covering said second end of said second wire for forming an electrochemical coupling to said second wire,
        a second dried electrolyte layer disposed covering said second electrochemically active layer, said second dried electrolyte layer when hydrated forming an aqueous solution including bicarbonate ions, and a second membrane having an outer surface exposed to the fluid in said measurement chamber and an inner surface covering said second electrolyte layer, said second membrane being sensitive to the difference in pH between the inner and outer surfaces thereof to form an electrical potential thereacross and being water and dissolved $CO_2$ permeable;

a ground electrode disposed in electrical contact with the fluid in said measurement chamber;

a reference electrode disposed in electrical contact with the fluid in said measurement chamber for providing a stable reference potential independent of ionic activity of the fluid in said reference chamber; and an electrical circuit connected to said first ends of said first and second wires including a first differential signal means connected to said first wire and said ground electrode for generating a first difference signal proportional to the electrical potential difference between said first wire and said ground electrode, a second differential signal means connected to said second wire and said ground electrode for generating a second difference signal proportional to the electrical potential difference between said second wire and said ground electrode, a third differential signal means connected to said reference electrode and said ground electrode for generating a third difference signal proportional to the electrical potential difference between said reference electrode and said ground electrode, a fourth differential signal means connected to said first differential signal means and said third differential signal means for generating a fourth difference signal proportional to the electrical potential difference between said first difference signal and said third difference signal, said fourth difference signal being said pH signal, a fifth differential signal means connected to said second and third differential signal means for generating a fifth difference signal proportional to the electrical potential difference between said second difference signal and said third difference signal, and a sixth differential signal means connected to said fourth differential signal means and said fifth differential signal means for generating a sixth difference signal proportional to the electrical potential difference between said fourth difference signal and said fifth difference signal, said sixth difference signal being said $CO_2$ signal.

2. The apparatus claimed in claim 1, wherein:
said first wire and said second wires are each composed of silver.

3. The apparatus claimed in claim 2, wherein:
said first and second electrochemically active layers are each composed of silver chloride.

4. The apparatus as claimed in claim 1, wherein:
said first dried electrolyte layer is composed of the dried residue of an aqueous solution of 0.024 molar 2-(n-morpholino) ethanesulfonic acid, 0.024 molar 2-(n-morpholino) ethanesulfonic acid - sodium salt and $5.0 \times 10^{-6}$ molar potassium chloride.

5. The apparatus claimed in claim 1, wherein:
said second dried electrolyte layer is composed of at least one salt which includes bicarbonate.

6. The apparatus claimed in claim 1, wherein:
said second dried electrolyte layer is composed of at least one salt which includes bicarbonate and a hydrophilic material in an amount for providing the degree of hydration desired upon rehydration.

7. The apparatus claimed in claim 1, wherein:
said second dried electrolyte layer is composed of the dried residue of an aqueous solution of 4% weight/volume polyvinyl alcohol having a molecular weight of 115,000 and 10% hydrolyzed, 0.0005 molar sodium chloride and 0.005 molar sodium bicarbonate.

8. The apparatus claimed in claim 1, wherein:
said first and second membranes are each composed of the dried residue of a solution of 32.8% polyvinyl chloride, 0.6% potassium tetrakis (4-chlorophenyl) borate, 65.6% bis (2-ethyl hexyl) sebacate, and 1.0% tridodecylamine by weight in an organic solvent.

9. The apparatus as claimed in claim 1, further comprising:
a reference solution chamber for containing a reference solution of known ion concentration in fluid communication with said measurement chamber; and
wherein said reference electrode is disposed in electrical contact with the fluid in said reference solution chamber.

10. The apparatus as claimed in claim 9, wherein:
said reference solution chamber includes a capillary section for fluid communication with said measurement chamber.

11. The apparatus claimed in claim 1, wherein:
said first, second, third, fourth, fifth and sixth differential signal means consist of respective differential amplifiers.

12. The apparatus as claimed in claim 1, wherein:
said first, second and third differential signal means consist of respective differential amplifiers; and
said fourth, fifth and sixth differential signal means includes
a conversion means connected to said said first, second and third differential signal means for generating respective first, second and third digital difference signals corresponding to said first, second and third difference signals, and
a digital processing system connected to said conversion means for forming said fourth difference signal by digital subtraction of said first digital difference signal and said third digital difference signal, said fourth difference signal being said pH signal, forming said fifth difference signal by digital subtraction of said second digital difference signal and said third digital difference signal, and forming said sixth difference signal by digital subtraction of said fifth difference signal and said fourth difference signal, said sixth difference signal being said $CO_2$ signal.

13. The apparatus as claimed in claim 12, wherein:
said conversion means includes
a first sample and hold circuit connected to said first differential signal means for sampling and holding said first difference signal,
a second sample and hold circuit connected to said second differential signal means for sampling and holding said second difference signal, a third sample and hold circuit connected to said third differential signal means for sampling and holding said third difference signal, a multiplexer having first, second and third inputs connected respectively to said first, second and third sample and hold circuits and having an output, for coupling a selected one of said first, second and third inputs to said output, and an analog to digital converter connected to said output of said multiplexer for generating a first digital difference signal when said multiplexer couples said first input to said output, a second digital difference signal when said multiplexer couples said second input to said output, and a third digital difference signal when said multiplexer couples said third input to said output; and said digital processing system includes a microprocessor control means connected to said analog to digital converter.

14. The apparatus as claimed in claim 13, further comprising:

an output means connected to said microprocessor control means for generating an operator perceivable indication of said pH signal and said $CO_2$ signal.

15. The apparatus claimed in claim 14, wherein:
said output means comprises a visual display means.

16. The apparatus claimed in claim 14, wherein:
said output means comprises a printer.

* * * * *